United States Patent
Poran et al.

(10) Patent No.: US 9,480,529 B2
(45) Date of Patent: *Nov. 1, 2016

(54) AESTHETIC TREATMENT DEVICE AND METHOD

(71) Applicant: S & Y ENTERPRISES LLC, West Orange, NJ (US)

(72) Inventors: Yehuda Poran, Hatzor Haglilit (IL); Oren Aharon, Haifa (IL)

(73) Assignee: S & Y ENTERPRISES LLC, West Orange, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/903,129

(22) Filed: May 28, 2013

(65) Prior Publication Data

US 2013/0345685 A1    Dec. 26, 2013

(30) Foreign Application Priority Data

Jun. 22, 2012    (EP) .................................... 12173261

(51) Int. Cl.
*A61B 18/20*    (2006.01)
*A61N 5/01*    (2006.01)
(Continued)

(52) U.S. Cl.
CPC ............. *A61B 18/20* (2013.01); *A61B 18/203* (2013.01); *A61N 5/01* (2013.01); *A61N 5/0616* (2013.01); *A61B 2017/00057* (2013.01); *A61B 2018/0047* (2013.01); *A61B 2018/00452* (2013.01);
(Continued)

(58) Field of Classification Search
CPC ................... A61N 5/0622; A61N 2005/0652; A61N 2005/0659; A61N 5/0613; A61N 5/0616; A61N 5/062; A61N 2005/067; A61N 5/0601; A61N 2005/0644; A61N 2005/0629; A61N 2005/063; A61N 5/0618; A61N 2005/007

See application file for complete search history.

(56) References Cited

U.S. PATENT DOCUMENTS 2,151,733 A    3/1939    Bonfield
4,622,971 A    11/1986    Yamamoto ............... 219/121.61
(Continued)

FOREIGN PATENT DOCUMENTS

DE                2157990        11/1971
WO    WO 2005/065565 A1    7/2005
(Continued)

OTHER PUBLICATIONS

Written Opinion of the International Searching Authority dated Dec. 22, 2014, issued to the corresponding International Application No. PCT/US2013/043507.
(Continued)

*Primary Examiner* — Lynsey Crandall
*Assistant Examiner* — Manolis Pahakis
(74) *Attorney, Agent, or Firm* — Stein IP, LLC

(57) ABSTRACT

An aesthetic treatment device including: a multi illumination system having at least one source in the visible region, disposed around a periphery of a predetermined area of skin; an imaging device, sensitive to the illumination system, to discern features on or in the skin within the predetermined area of skin to be treated; multiple treatment light sources mounted on an optical bench and aimed and focused to a point of treatment within the predetermined area of skin; a mechanical guidance system to guide the multiple treatment light sources; and a pulse generator to control power output of the multiple treatment light sources based upon the treatment to be applied to the predetermined area of skin.

19 Claims, 3 Drawing Sheets

(51) Int. Cl.
*A61N 5/06* (2006.01)
*A61B 18/00* (2006.01)
*A61B 17/00* (2006.01)

(52) U.S. Cl.
CPC ............... *A61B2018/00476* (2013.01); *A61B 2018/00642* (2013.01); *A61B 2018/00904* (2013.01); *A61B 2018/2065* (2013.01); *A61N 2005/0644* (2013.01)

(56) References Cited

U.S. PATENT DOCUMENTS

| | | | |
|---|---|---|---|
| 4,905,690 A | 3/1990 | Ohshiro | 607/89 |
| 4,930,504 A * | 6/1990 | Diamantopoulos et al. | 607/88 |
| 5,054,502 A * | 10/1991 | Courage | 600/587 |
| 5,146,923 A * | 9/1992 | Dhawan | 600/476 |
| 5,198,875 A * | 3/1993 | Bazin et al. | 356/369 |
| 5,533,266 A * | 7/1996 | Kelman | A61B 18/203 132/200 |
| 5,551,949 A * | 9/1996 | Kim | 601/15 |
| 5,807,387 A | 9/1998 | Druais | 219/121.78 |
| 5,820,625 A * | 10/1998 | Izawa | A61B 18/203 606/13 |
| 5,851,181 A * | 12/1998 | Talmor | A61B 5/0071 600/407 |
| 5,993,440 A * | 11/1999 | Ghassemi | B26B 19/00 30/41.5 |
| 6,019,482 A | 2/2000 | Everett | 362/184 |
| 6,032,071 A * | 2/2000 | Binder | 600/476 |
| 6,050,990 A * | 4/2000 | Tankovich | A61B 18/203 606/16 |
| 6,081,612 A * | 6/2000 | Gutkowicz-Krusin et al. | 382/128 |
| 6,210,425 B1 * | 4/2001 | Chen | A61N 5/062 600/436 |
| 6,402,739 B1 * | 6/2002 | Neev | A61B 18/203 606/13 |
| 6,413,267 B1 * | 7/2002 | Dumoulin-White et al. | 607/89 |
| 6,451,007 B1 * | 9/2002 | Koop | A61B 18/20 128/898 |
| 6,702,837 B2 | 3/2004 | Gutwein | 606/9 |
| 6,736,807 B2 * | 5/2004 | Yamazaki et al. | 606/9 |
| 6,872,221 B2 | 3/2005 | Lytle | 128/898 |
| 6,976,984 B2 * | 12/2005 | Cense | A61B 18/203 606/10 |
| 7,006,223 B2 * | 2/2006 | Mullani | 356/369 |
| 7,097,639 B1 * | 8/2006 | Almeida | A61B 18/203 128/898 |
| 7,151,956 B2 * | 12/2006 | Satoh | A61B 5/0059 348/E5.029 |
| 7,204,832 B2 * | 4/2007 | Altshuler | A45D 26/0061 606/22 |
| 7,214,222 B2 * | 5/2007 | Yamazaki et al. | 606/9 |
| 7,220,254 B2 | 5/2007 | Altshuler | 128/898 |
| 7,328,060 B2 * | 2/2008 | Mooradian et al. | 600/476 |
| 7,369,692 B2 * | 5/2008 | Shirai et al. | 382/128 |
| 8,821,482 B2 * | 9/2014 | Verhagen et al. | 606/9 |
| 2001/0053907 A1 * | 12/2001 | Ota | A61B 18/203 606/10 |
| 2003/0026110 A1 * | 2/2003 | Satoh et al. | 362/572 |
| 2003/0036751 A1 * | 2/2003 | Anderson | A61B 5/0059 606/9 |
| 2003/0050561 A1 * | 3/2003 | Bazin | A61B 5/448 600/476 |
| 2003/0199859 A1 * | 10/2003 | Altshuler | A61B 18/203 606/9 |
| 2003/0216719 A1 | 11/2003 | Debenedictis | 606/10 |
| 2004/0015156 A1 * | 1/2004 | Vasily | 606/9 |
| 2004/0082940 A1 | 4/2004 | Black | 606/9 |
| 2004/0210277 A1 | 10/2004 | Becker | 607/88 |
| 2004/0225339 A1 * | 11/2004 | Yaroslavsky | A61N 5/0616 607/88 |
| 2005/0045189 A1 * | 3/2005 | Jay | A61B 5/0059 128/898 |
| 2005/0154382 A1 | 7/2005 | Altshuler et al. | 606/9 |
| 2006/0247741 A1 | 11/2006 | Hsu | 607/88 |
| 2007/0049910 A1 * | 3/2007 | Altshuler | A61B 18/203 606/9 |
| 2007/0060819 A1 * | 3/2007 | Altshuler | A61B 5/0059 600/475 |
| 2007/0213791 A1 * | 9/2007 | Van Hal | A61B 18/203 607/89 |
| 2007/0255355 A1 * | 11/2007 | Altshuler | A61B 18/203 607/86 |
| 2008/0077198 A1 * | 3/2008 | Webb et al. | 607/88 |
| 2008/0255548 A1 * | 10/2008 | Van Hal | A61B 18/203 606/10 |
| 2008/0294151 A1 * | 11/2008 | Whitaker et al. | 606/9 |
| 2009/0088824 A1 | 4/2009 | Baird | 607/90 |
| 2009/0099559 A1 | 4/2009 | Dhadwal | 606/9 |
| 2010/0049177 A1 | 2/2010 | Boone, III et al. | 606/9 |
| 2011/0137303 A1 * | 6/2011 | Dolleris et al. | 606/17 |
| 2011/0160712 A1 | 6/2011 | Tankovich | 606/9 |
| 2012/0041283 A1 | 2/2012 | Krishnan | 600/306 |
| 2012/0123444 A1 * | 5/2012 | Verhagen | A61B 18/20 606/133 |
| 2012/0283803 A1 * | 11/2012 | Liu et al. | 607/89 |
| 2012/0296322 A1 * | 11/2012 | Yamazaki et al. | 606/9 |
| 2014/0081148 A1 * | 3/2014 | Heinrich | G01N 21/21 600/476 |
| 2014/0296837 A1 * | 10/2014 | Varghese | A61B 5/448 606/9 |
| 2015/0080866 A1 * | 3/2015 | Verhagen | B26B 19/38 606/9 |
| 2015/0202006 A1 * | 7/2015 | Johnson | A61B 18/203 606/9 |
| 2015/0298254 A1 * | 10/2015 | Varghese | A61B 18/203 30/34.2 |
| 2015/0359592 A1 * | 12/2015 | Moeskops | A61B 18/203 606/9 |

FOREIGN PATENT DOCUMENTS

| | | |
|---|---|---|
| WO | WO 2006/044652 A1 | 4/2006 |
| WO | WO 2008/124839 A1 | 10/2008 |
| WO | WO 2009/155501 A2 | 12/2009 |
| WO | WO 2011/116347 A1 | 9/2011 |
| WO | WO 2011/154227 A1 | 12/2011 |
| WO | WO 2012/106678 A1 | 8/2012 |

OTHER PUBLICATIONS

Written Opinion of the International Preliminary Examining Authority dated Dec. 31, 2014, issued to the corresponding International Application No. PCT/US2013/043507.
International Search Report dated Oct. 28, 2013, issued to International Application No. PCT/US2013/043507.
U.S. Non-Final Office Action dated Sep. 16, 2015, issued to the corresponding U.S. Appl. No. 14/137,116.
International Preliminary Report on Patentability dated Aug. 20, 2015, issued to International Application No. PCT/US2013/043507.

* cited by examiner

AESTHETIC TREATMENT DEVICE AND METHOD

CROSS-REFERENCE TO RELATED APPLICATIONS

This application claims the benefit of European Application No. 12173261.4, filed on Jun. 22, 2012, in the European Patent Office.

BACKGROUND OF THE INVENTION

1. Field of the Invention

Aspects of the invention relate to a miniature device which performs aesthetic treatments such as acne treatment, wrinkle removal, hair removal, rejuvenation and other applications based on light treatment. The system may comprise a detection system which evaluates the exact area to be treated and a multiple wavelength laser or LED sources tuned to optimally treat the unwanted aesthetic disorder and aimed at a single point from different directions.

2. Description of the Related Art

In known aesthetic treatment devices, treatment is performed by flooding a relatively large area of skin with light without differentiation between healthy skin and the area to be treated. A typical system for dermatological treatment is described in US Patent Publication No. 2009/0054880 A1 intended to perform dermatological treatment by intense pulses of light radiated over large skin areas. The treatment selection is performed by chromatic characteristics of the skin or hair follicles and selection between treated and not to be treated areas is performed by the light source wavelength selection in a process called photo thermolysis or wavelength depended light absorption.

Light is absorbed by dark objects, so laser energy can be absorbed by dark material in the skin, but with higher speed and intensity. This dark target matter, or chromophore, can be naturally-occurring or artificially introduced. The main drawback of this procedure is that large areas of skin are unnecessarily exposed to high levels of intense pulsed light with potential adverse results.

For example, conventional laser hair removal systems rely on flooding large areas with high intensity light, hair removal is performed at wavelengths that will not damage the human tissue, such that the light will be transmitted by the skin to the follicle depth and destroy the follicle by photothermolysis.

SUMMARY OF THE INVENTION

Since small features on the skin surface are difficult to discern due to lack of contrast, especially when the colors of feature and skin surrounding are similar, a special peripheral illumination system is disclosed which greatly improves the contrast.

A specialized illumination technique that capitalizes on oblique illumination enhancing the image contrast is disclosed. This contrast enhancement technology is especially applicable in discerning small features with low contrast, such as blonde or white hair on top of pale skin. The illumination increases contrast by two mechanisms; oblique illumination (about 90 degrees to the optical axis of a camera) and multiple wavelength illumination from UV to infrared, each providing complimentary color to a given feature. Light passing through a glass substrate will be reflected only from non-uniform features on the skin surface, illumination from oblique angles at all azimuths is diffracted, refracted, and reflected towards the camera objective to form a bright image of the specimen superimposed onto a primarily dark background.

A special imaging device with sensitivity matching the light sources will be used to detect and discern the areas to be treated from the surrounding areas. A second optional visible illumination light source will be used to illuminate the skin surface for positioning and image display. Selection of areas to be treated will be performed by spatial discernment rather than wavelength chromatic selection.

The treating source will comprise a laser or an LED with an appropriate wavelength dedicated to a specific treatment application. Preferably, the light source will be a dual wavelength laser capable of performing treatment by being transmitted through the skin or by local skin penetration. The system's laser power is sufficient to produce a beam capable of penetrating the epidermis and destroying a selected target. Penetration is achieved by selecting the right wavelength to be transmitted by the skin to the target area or alternatively by increasing power density to levels that will locally perforate the epidermis and destroy targets for example, hair follicles, color pigment stains and other skin disorders such as wrinkles. A special controllable power supply will allow operation of a treatment light source under a continuous or a pulse light mode. The laser beam used in laser rejuvenation and wrinkles removal will be targeted at the wrinkle outline. It simultaneously heats the underlying skin, called the dermis. This action works to stimulate growth of new collagen fibers. As the treated area heals, the new skin that forms is smoother and firmer. As for acne, a different wavelength source will be used, usually in the 400 nm region combined with a longer wavelength for heating the underlying skin.

Acne occurs when the body begins producing an overabundance of oils and sebaceous fluids that become trapped beneath the surface due to cuticle build up or debris. When this happens, unnatural levels of bacteria can begin to form, which can trigger infections.

Laser systems will be arranged to converge on a spot from different directions, creating a powerful spot of multi wavelength lasers on one hand and a highly diverging beam on the other hand, thereby improving the system safety. A special smart guiding mechanical system is provided for accurately selecting the area to be treated with micron accuracy.

One feature of uniqueness of the present aesthetic treatment device is that this device achieves and sometimes overcomes the performance of the systems existing in the market for the above procedures, while integrating all the capabilities of aesthetic treatment in a miniature hand held apparatus. The treatment apparatus is based on multiple light sources, lasers or LEDs focused on the treatment area from different directions. The multiple light sources for treatment purposes could have the same wavelength or different wavelengths each optimized for a different application. Target selection is performed by a dual wavelength smart illumination system. An internal light source structure enables the aesthetic treatment device to operate with high peak intensity for effective treatment, while the emission spectrum remains mostly in the near infra-red region. Aiming the multiple focused beams to target is performed manually or automatically.

Due to the above features, the proposed aesthetic treatment device is potentially usable for all hair types since its working principle is based on spatial hair removal rather than selective photothermolysis.

Another advantage of the proposed aesthetic treatment device is that the same provides an image display of the working area near and around the light sources, enabling treatment directly by a user even in concealed areas.

In addition, the high source focus ability and miniature size enables the use of a well designed miniature treatment hand piece.

Many disadvantages of prior art aesthetic treatment devices are advantageously solved by aspects of the present invention. A partial list is as follows:

In prior art systems a high power light or laser is applied to a relatively large area and the required treatment is usually achieved by photothermolysis followed by collateral damage to the surrounding skin. It is an aspect of the present invention to overcome this drawback by applying a focused laser beam or light directly to the treatment location without affecting the surrounding skin.

Some prior art treatments are performed by selective photothermolysis or by skin limited transparency to allow deep light penetration. It is another aspect of the present invention to perform treatment by spatial recognition of an area to be treated, enabling focused treatment and potential treatment, not only by photothermolysis but by a direct localized system.

In some prior art devices, the irradiated area is discernible only by visible illumination from above with poor image contrast in some cases, yet aspects of the present invention art provide an additional peripheral illumination which improves the contrast of features on the skin surface.

In some prior art devices, the light source is relatively large, requiring a large amount of power and complicated power electronics. It is another aspect of the present invention to provide a miniature treatment laser or LED with low power requirements, and which potentially is operated from a USB power source.

In some prior art devices, the light source is usually a single light source per treatment handle and in the case of a laser hand piece, the light radiates in a very limited light spectrum of a few nanometers. It is another aspect of the present invention to overcome these by using a dual wavelength miniature laser or mounting several lasers or an LED at the same treatment laser head for improved efficacy.

According to an aspect of the present invention, a miniature aesthetic treatment device discerns features to be treated on a skin surface by a peripheral illumination system based on multiple low power wavelength LED sources and is equipped with multiple high power wavelength light sources intended for therapeutic purposes directed to the features to be treated. The multiple high power wavelength light sources are preferable to a dual wavelength laser diode equipped with a focusing element. The multiple high power light sources are preferably mounted on a mechanical device serving as an optical bench and are aimed to have a point of intersection. A mechanical guidance system and an imaging device are provided to guide the focused laser energy to the treatment point on or under the skin surface.

There is provided in accordance with an embodiment of the present invention, an aesthetic treatment device comprising: a multi illumination system having at least one source in the visible region, disposed around a periphery of a predetermined area of skin; an imaging device, sensitive to the illumination system, to discern features on or in the skin within the predetermined area of skin to be treated; multiple treatment light sources mounted on an optical bench and aimed and focused to a point of treatment in the predetermined area of skin; a mechanical guidance system to guide the multiple treatment light sources; a pulse generator to control power output of the multiple treatment light sources based upon the treatment to be applied to the predetermined area of skin.

According to an embodiment, the multiple treatment light sources are of different wavelengths enabling different aesthetic procedures to be applied as the treatment.

According to an embodiment, the mechanical guidance system comprises a base having at least one spherical portion and a body which is manually operable about the at least one spherical portion, to manually operate the aesthetic treatment device in near spherical movements.

According to an embodiment, the mechanical guidance system comprises a motor to move the mechanical guidance system, and the aesthetic treatment device further comprises a dedicated computerized controller to control the motor.

According to an embodiment, the aesthetic treatment device further comprises a moving focusing optical system to create different beam sizes of the light sources based upon the treatment to be applied to the predetermined area of the skin treated by the treatment light sources.

According to an embodiment, the aesthetic treatment device further comprises a registration device to mark treated areas.

There is provided in accordance with another embodiment of the present invention, a method for a dermatological aesthetic treatment with a device comprising: illuminating a predetermined skin area using multiple light sources around a periphery of the predetermined skin area, the multiple light sources having at least one source in the visible region; discerning a feature on or in the predetermined area of the skin by generating an image of the feature illuminated by the multiple light sources; and controlling power output of treatment light sources to perform treatment on the feature.

According to an embodiment, the controlling of the power output of the treatment light sources comprises generating different wavelengths of light between the treatment light sources based upon the treatment to be performed.

According to an embodiment, the method further comprises moving the treatment light sources spherically about a base having at least one spherical portion.

According to an embodiment, the method further comprises moving the treatment light sources using a motor.

According to an embodiment, the controlling of the power output of the treatment light sources comprises generating different beam sizes between the treatment light sources.

According to an embodiment, the method further comprises marking the predetermined area of skin treated.

Additional aspects and/or advantages of the invention will be set forth in part in the description which follows and, in part, will be obvious from the description, or may be learned by practice of the invention.

BRIEF DESCRIPTION OF DRAWINGS

These and/or other aspects and advantages of the invention will become apparent and more readily appreciated from the following description of the embodiments, taken in conjunction with the accompanying drawings of which.

DETAILED DESCRIPTION OF EMBODIMENTS

Figure 1:
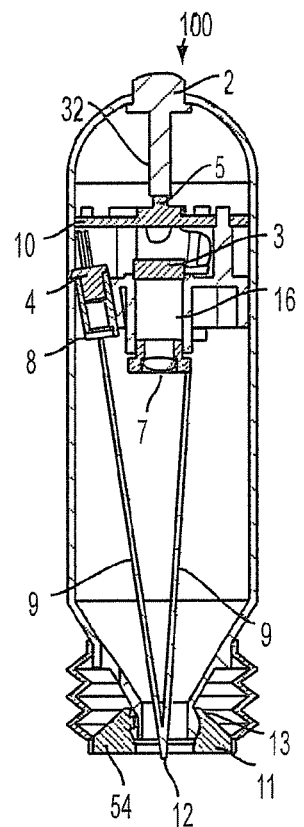
FIG. 1 is schematic representation of an aesthetic treatment device according to an embodiment of the present invention.

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Aspects of the present invention disclose an aesthetic treatment device enabling application of focused light beams directly to skin disorders, including miniature ones like hair follicles, stains, wrinkle lines, tattoo particles, miniature veins, etc., by treating the disorder with minimal or no effect on the surrounding skin.

Aspects of the present invention disclose an aesthetic treatment device enabling recognition of areas of skin to be treated. Recognition of the disorder is performed by a dual illumination system and the application of coherent or noncoherent multiple focused light sources directly to a specific recognized target for aesthetic treatments.

Aspects of the present invention disclose a dual illumination system, such that an additional illumination system is provided in addition to a "regular" illumination system. The so called regular illumination system illuminates the skin from above and it is mounted around a camera lens. The configuration usually results in good illumination for the skin, but due to back reflections, hair and hair roots are not easily seen. The additional illumination system is mounted on a peripheral area of a system opening as shown in the relevant drawing, and provides illumination which is parallel to the skin. Features protruding out from the skin will be strongly illuminated while the skin will remain in relative darkness, creating an improved image emphasizing hair and outer surface features.

FIG. 1 is a schematic representation of an aesthetic treatment device 100. An imaging apparatus 16 includes a camera system 7 and a miniature imaging device 3 (see FIGS. 1 and 2). The camera system 7 is a multispectral camera system sensitive to the visible spectrum and infrared spectrum. The miniature imaging device 3, preferably, but not necessarily, a charge coupled device CCD, receives the images obtained by the camera system 7, and provides a visual of the images obtained by the camera system 7 for viewing by a user. The aesthetic treatment device 100 may be connected to a computer screen, a tablet or a cell phone, or a regular screen like a television screen, wirelessly or through a USB or other connection element, or connected to an analog screen via a connector cable or other connection element. An illumination system 11, in this instance, LEDs or miniature lamps, are disposed in the peripheral area of the skin of a person to be treated (either the user or another party). The immerging illumination is primarily parallel to the skin surface, thereby improving the contrast of different features on the skin surface. Treatment light sources, such as laser modules 40, each having a laser diode 4 and focusing optics 8, are mounted on a miniature optical bench 6, with each laser diode 4 having a focused beam 9 and aimed at the same aiming point 12 on or under the skin. Each laser diode 4 sits in a housing such that the housing sits inside the miniature optical bench 6, and the miniature optical bench 6 has the necessary electronics (e.g., an electronic chip) to drive the laser diode 4.

Figure 3:
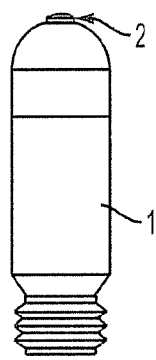
FIG. 3 is a view of the outer surface of the aesthetic treatment device shown in FIG. 1.
Figure 4:
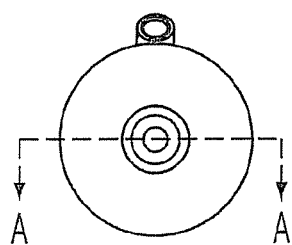
FIG. 4 is a cross-sectional view of the aesthetic treatment device shown in FIG. 1 along line A-A, revealing a bottom up view of the aesthetic treatment device.
Figure 5:
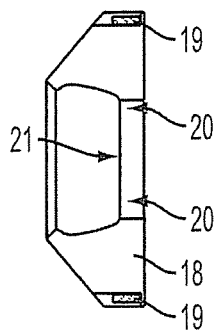
FIGS. 5-9 are blown up views showing an illumination system according to one embodiment of the aesthetic treatment device shown in FIG. 1.
Figure 6:
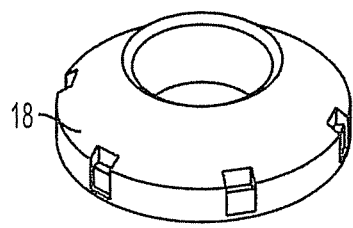

The LEDs 4 may have different wavelengths. The aesthetic treatment device 100 is equipped with a firing button 2 which is exposed and protrudes externally from the outer surface 1 of the aesthetic treatment device 100 (see FIG. 3), and a firing contact 5 connected to the firing bottom 2 by a connecting element 32. A pulse pattern of the LEDs is either predetermined in advance, such as at the factory, or may be selected by a user via software which is accessible to the user. By pushing the firing bottom 2, the firing contact 5 moves to activate the laser modules 40, to produce the predetermined pulse pattern or pulse duration. A special spherical bearing 13 pivots and thus scans the focused beams 9 across the skin surface. The user, who is performing hair removal or rejuvenation by self-activating the aesthetic treatment device 100 or performing hair removal or rejuvenation on another person, moves the upper part of the aesthetic device 100 (outer surface 1) around the spherical bearing 13 to provide a delicate laser movement at the skin surface. In FIG. 4, line A-A shows a cross-section of the aesthetic treatment device 100 where the concentric circles represent an elastic element sealing the spherical bearing 13. Moving the outer surface 1 manually around the spherical bearing 13 will steer the LEDs 4 to different locations. Scanning of the aiming point 12 is provided by manually moving the aesthetic treatment device 100 around such a pivot.

The treatment lasers or LEDs 4 are equipped with the focusing optics 8 to adjust beam size by moving up and down of the focused beams 9 which are directed towards the specific treatment skin area, then performing localized treatment without significant damage to the surrounding skin area. A registration device 54 is for registration purposes for the user to be able to mark and register the areas he/she has already treated.

An electronics board 10 includes a control unit and a pulse generator. The control unit controls beam parameters to be applied to the skin. Control is performed through the pulse generator and performs intensity duration as required for a particular aesthetic skin treatment. The pulse generator can be operated by the user pressing the firing button 2, the user can select the power by software loaded on a computing device or can have the power displayed on a TV screen, and some separate device to control the power.

Figure 2:
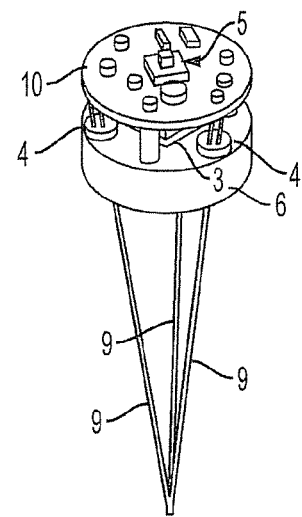
FIG. 2 is a blown up peripheral view of a portion of the aesthetic treatment device shown in FIG. 1.
Figure 7:
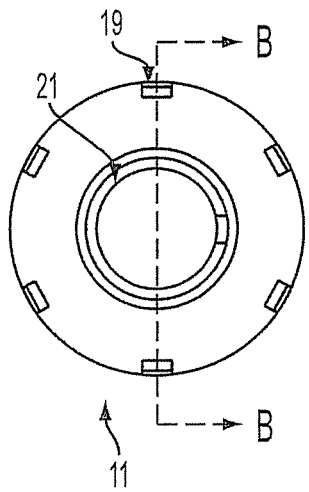
Figure 8:
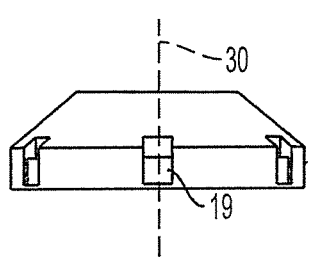
Figure 9:
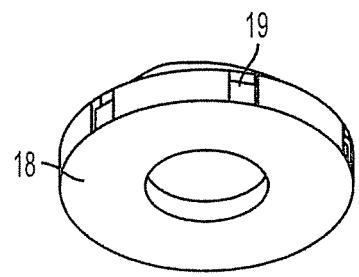
Figure 10:
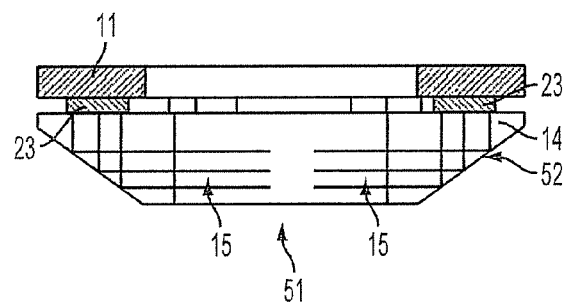
FIGS. 10-13 are blown up views showing an illumination system according to another embodiment of the aesthetic treatment device shown in FIG. 1.
Figure 11:
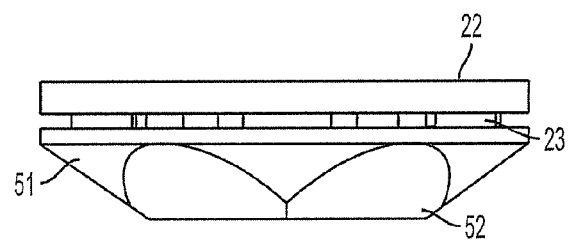
Figure 12:
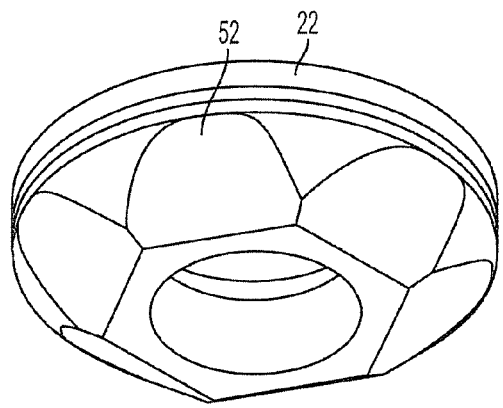

FIGS. 5-9 are blown up drawings of the illumination system 11 shown in FIG. 1. FIG. 2 reveals the basics of the illumination system 11. The proposed illumination system 11 includes a glass disk (substrate) 18 with illumination sources 19 at its perimeter. Illumination sources 19 output light of different wavelengths and can be controlled individually. The different wavelengths can provide for a better contrast between the skin surface and the area (skin features) to be treated. Light 20 travels in the glass disk substrate 18 almost perpendicular to a system optical axis 30, thus providing oblique illumination to the skin features to be observed. Here, the light output by the illumination sources 19 travels close to parallel to the skin. An inner aperture, of the glass disk substrate 18 can be a hollow 21 as shown in this configuration or solid. The illumination system 11 illuminates the area of the skin just underneath the circumference of the hollow (the area "within" the hollow) and the LEDs 4 treat the area of skin within the hollow to fix the aesthetic problem which is revealed therein. FIG. 7 is a view of the illumination system 11 along line B-B of the aesthetic treatment device 100 (a bottom up view).

Figure 13:
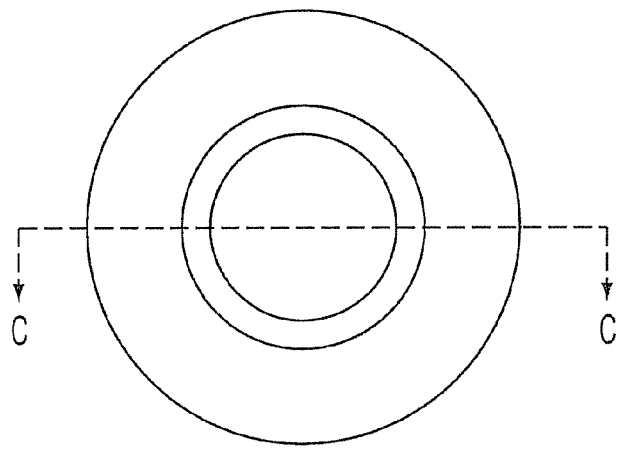

FIGS. 10-13 show a blown up section of an illumination system 51 according to another embodiment where illumination sources 23 are mounted on a printed circuit board 22 illuminating a transparent part 14 having reflective surfaces 52. The reflective surfaces 52 reflect light by 90 degrees, causing a light beam 15 to emerge almost parallel to the skin surface from the opening in the reflective surfaces 52. Thus unlike in FIGS. 5-9 where the illumination sources 19 are mounted on a periphery of a glass disk substrate 18 and light is emitted nearly parallel to the skin, in FIGS. 10-13, the illumination sources 23 direct light perpendicular to the skin and the reflective surfaces bend the light 90 degrees so as to be parallel to the skin. FIG. 13 is a view of the illumination system 5 (along C-C of the aesthetic treatment device 100 (a bottom up view).

Accordingly, a device and method of an aesthetic treatment device 100 is disclosed. The device includes multiple focused beams to be selectively aimed at the area of the skin to be treated. Aspects of the present invention relate to a method for aesthetic treatment where multi wavelength light sources combined with an adequate imaging device is used to select the target skin area and an appropriate laser light combination is used to treat the skin area target. The treatment is performed by aiming focused light sources or laser beams on or under the skin which are powerful enough to penetrate and destroy hair follicles which are under the skin, treat acne and treat other dermatological disorders on or under the skin. More specifically, aspects of the present invention relate to a miniature aesthetic treatment device 100 capable of performing non-contact treatment to a limited area of the skin of a person, to treating dermatological disorders such as hair follicles, acne glands, tattoo removal, wrinkles, age stains, rejuvenation and other superficial dermatological treatments. The imaging device 16 is capable of recognizing the area to be treated using an effective illumination device, such as the illumination system 11, illuminating the area of the skin to be treated from its periphery, thereby improving the contrast between the skin and skin surface disorders.

Known methods use a relatively large light source with a specific wavelength range, which floods a large skin area, the light source being capable of selective treatment by photothermolysis. For example, hair removal is based on the principle of selectively heating and destroying the hair follicle while avoiding significant damage to surrounding skin or tissue. Hair follicles are selected by photothermolysis, which is a method based on the fact that hair absorbs greater amounts of light, due to its darker color when compared with surrounding skin tissue, and a similar mechanism will work for other treatments such as skin stains and miniature overexposed veins. Hair is thus automatically selected by the light since it has a darker color and thus higher absorption coefficient. On the other hand, hair or other skin disorders brighter than the surrounding skin area are difficult if not impossible to treat by prior art techniques. It is a purpose of the aesthetic treatment device according to an embodiment of the present invention to offer a different method based on spatial selection of hair follicles or other targets, destroying the follicle by focused light energy with little to no damage or exposure to surrounding skin or tissue.

One of the main limitations of existing methods is the usage of the photothermolysis effect which relies on color difference between normal skin and the area to be treated, where a basic requirement is for the skin to be significantly brighter than the hair follicle or glands or and basically transparent to the used wavelength. That is the main reason that light colored (such as blonde) and white hair are almost impossible to treat using existing devices and methods since they are brighter than the surrounding skin. It is a purpose of this invention to offer a solution free of those prior art limitations.

Aspects of this invention relate generally to an aesthetic treatment device and method to detect the position of a small area of skin to be treated and focus a light source on the specific area (on or under the skin) without affecting, and damaging the surrounding skin area.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. An aesthetic treatment device for treatment of a predetermined area of skin by contacting a surface of the skin, the aesthetic treatment device comprising:
   a handpiece comprising:
      an optical bench;
      multiple treatment laser modules configured to emit laser beams having different wavelengths, and mounted on a circumference of the optical bench;
      focusing optics configured to focus the multiple laser beams to a focal point where the multiple laser beams intersect under the skin;
      an imaging device having an optical axis; and
      a bearing comprising a spherical portion;
   a illumination system configured to lie on the predetermined area of skin during the treatment, the illumination system having an aperture along the optical axis that enables the multiple laser beams to reach the focal point under the skin, wherein the illumination system has multiple illumination light sources disposed around a periphery of the aperture and configured to emit and propagate multiple illumination beams having different wavelengths in the UV to infrared range across the aperture over the predetermined area of skin and in a parallel direction to the skin surface, wherein the imaging device is configured to detect the wavelengths of the multiple illumination beams of the illumination system and is configured to discern features on or under the predetermined area of skin within the aperture, wherein the bearing is configured to allow for scanning the focal point across the predetermined area of skin by manually pivoting the handpiece relative to the illumination system;
and
   a pulse generator to control power output of the multiple treatment laser modules based upon the treatment to be applied to the predetermined area of skin.

2. The aesthetic treatment device according to claim 1, wherein the bearing allows for spherical movements in said pivoting.

3. The aesthetic treatment device according to claim 1, further comprising a moving focusing optical system to create different beam sizes of the laser beams based upon the treatment to be applied to the predetermined area of the skin treated by the multiple treatment laser modules.

4. The aesthetic treatment device according to claim 1, further comprising a registration device to mark treated areas of the skin surface.

5. The aesthetic treatment device according to claim 1, wherein, the multi illumination system comprises a disk with the aperture in a middle thereof.

6. The aesthetic treatment device according to claim 5, wherein, the disk comprises reflective surfaces configured to reflect the multiple illumination beams in the direction parallel to the skin surface.

7. The aesthetic treatment device according to claim 1:
wherein the illumination system further comprises a printed circuit board on which the multiple illumination light sources are mounted.

8. The aesthetic treatment device according to claim 5, wherein, the aperture of the disk has spherical walls configured to allow pivoting around the spherical portion of the bearing.

9. The aesthetic treatment device according to claim 1, wherein the imaging device is at a position in line with a center of the orifice.

10. A method for a dermatological aesthetic treatment comprising:
providing the aesthetic treatment device of claim 1;
illuminating the predetermined skin area using the illumination system;
discerning a feature on or in the predetermined area of the skin by generating an image of the feature illuminated by the illumination system; and
controlling the power output of the treatment laser modules to perform treatment on the feature.

11. The method according to claim 10, wherein the controlling of the power output of the treatment laser modules comprises generating the different wavelengths between the treatment laser modules based upon the treatment to be performed.

12. The method according to claim 10, further comprising moving the treatment light sources spherically about a the spherical portion.

13. The method according to claim 10, wherein the controlling of the power output of the treatment light sources comprises generating different beam sizes between the treatment laser modules.

14. The method according to claim 10, further comprising marking the predetermined area of skin treated.

15. A method for performing an aesthetic treatment on a predetermined area of skin, comprising:
providing the aesthetic treatment device of claim 1;
illuminating the multiple illumination beams with at least one being in the visible range parallel to the predetermined area of the skin;
generating an image of the illuminated predetermined area of the skin;
adjusting the power output of the multiple treatment laser modules to perform the treatment based upon the image of the illuminated predetermined area of the skin.

16. The method of claim 15, wherein the illuminating the multiple illumination beams comprises:
directing the illumination beams, originated from a periphery of the predetermined area of skin and the periphery of the illumination system, toward a central point within the aperture to illuminate the predetermined area of skin.

17. The method of claim 16, where the illuminating further comprises initially directing the illumination beams in a direction perpendicular to the predetermined area of skin and then reflecting the illuminating light beams 90 degrees to be parallel to the predetermined area of skin.

18. A method for performing an aesthetic treatment on a predetermined area of skin, comprising:
providing the aesthetic treatment device of claim 1;
illuminating the predetermined area of skin with the illumination system;
generating an image of the illuminated predetermined area of the skin; and
adjusting the power output of the multiple treatment laser modules having different wavelengths to simultaneously perform the treatment based upon the image of the predetermined area of the skin.

19. The method according to claim 18, further comprising adjusting beam sizes of the multiple treatment laser modules.

* * * * *